(12) United States Patent
Mujaj et al.

(10) Patent No.: US 12,329,980 B2
(45) Date of Patent: Jun. 17, 2025

(54) MEDICAL DEVICE COMPONENT WITH DUAL-BAND COIL ASSEMBLY

(71) Applicant: Cochlear Limited, Macquarie University (AU)

(72) Inventors: Adam Mujaj, Redfern (AU); Werner Meskens, Opwijk (BE)

(73) Assignee: Cochlear Limited, Macquarie University (AU)

( * ) Notice: Subject to any disclaimer, the term of this patent is extended or adjusted under 35 U.S.C. 154(b) by 1131 days.

(21) Appl. No.: 17/273,180

(22) PCT Filed: Nov. 27, 2019

(86) PCT No.: PCT/IB2019/060239
§ 371 (c)(1),
(2) Date: Mar. 3, 2021

(87) PCT Pub. No.: WO2020/115614
PCT Pub. Date: Jun. 11, 2020

(65) Prior Publication Data
US 2021/0322776 A1    Oct. 21, 2021

Related U.S. Application Data

(60) Provisional application No. 62/774,365, filed on Dec. 3, 2018.

(51) Int. Cl.
*H02J 50/00*    (2016.01)
*A61N 1/36*    (2006.01)
(Continued)

(52) U.S. Cl.
CPC ....... *A61N 1/3787* (2013.01); *A61N 1/36038* (2017.08); *A61N 1/37211* (2013.01); *H02J 50/10* (2016.02); *H02J 50/90* (2016.02)

(58) Field of Classification Search
CPC .................. H02J 50/10; H02J 50/90
(Continued)

(56) References Cited

U.S. PATENT DOCUMENTS 9,136,728 B2    9/2015    Dinsmoor et al.
9,912,197 B2    3/2018    Riehl
(Continued)

FOREIGN PATENT DOCUMENTS

KR    10-2017-0109894 A    10/2017

OTHER PUBLICATIONS

International Search Report and Written Opinion in counterpart International Application No. PCT/IB2019/060239, mailed Mar. 19, 2020, 12 pages.
(Continued)

*Primary Examiner* — Nathaniel R Pelton
(74) *Attorney, Agent, or Firm* — Edell, Shapiro & Finnan, LLC

(57) ABSTRACT

Presented herein are techniques that provide an external component of an implantable medical device system with the ability to use a single inductive coil assembly to both receive charging signals from an inductive charger and for bi-directional transcutaneous communication with an implantable component. In particular, an external component comprises a coil assembly comprising a first coil segment and a second coil segment. The first and second coil segments have a first electrically connected arrangement that is used to receive charging signals, and a second electrically connected arrangement that is used for the bi-directional transcutaneous communication.

23 Claims, 9 Drawing Sheets

(51) Int. Cl.
*A61N 1/372* (2006.01)
*A61N 1/378* (2006.01)
*H02J 50/10* (2016.01)
*H02J 50/90* (2016.01)

(58) Field of Classification Search
USPC .......................................................... 320/108
See application file for complete search history.

(56) References Cited

U.S. PATENT DOCUMENTS

| | | |
|---|---|---|
| 9,960,628 B2 | 5/2018 | Peralta et al. |
| 2012/0262108 A1 | 10/2012 | Olson et al. |
| 2014/0055088 A1* | 2/2014 | Joshi ....................... H02J 50/80 |
| | | 320/108 |
| 2014/0257432 A1* | 9/2014 | Tahmasian ......... A61N 1/37223 |
| | | 607/59 |
| 2017/0126063 A1 | 5/2017 | Pan et al. |
| 2018/0131241 A1 | 5/2018 | Hornung et al. |
| 2018/0262037 A1 | 9/2018 | Meskens |

OTHER PUBLICATIONS

Bocan, Kara N. et al., "Adaptive Transcutaneous Power Transfer to Implantable Devices: A State of the Art Review", Mar. 18, 2016, 23 pages.
Ali, Hussnain et al., "Inductive Link Design for Medical Implants", 2009 IEEE Symposium on Industrial Electronics and Applications (ISIEA 2009), Oct. 4-6, 2009, 6 pages.

\* cited by examiner

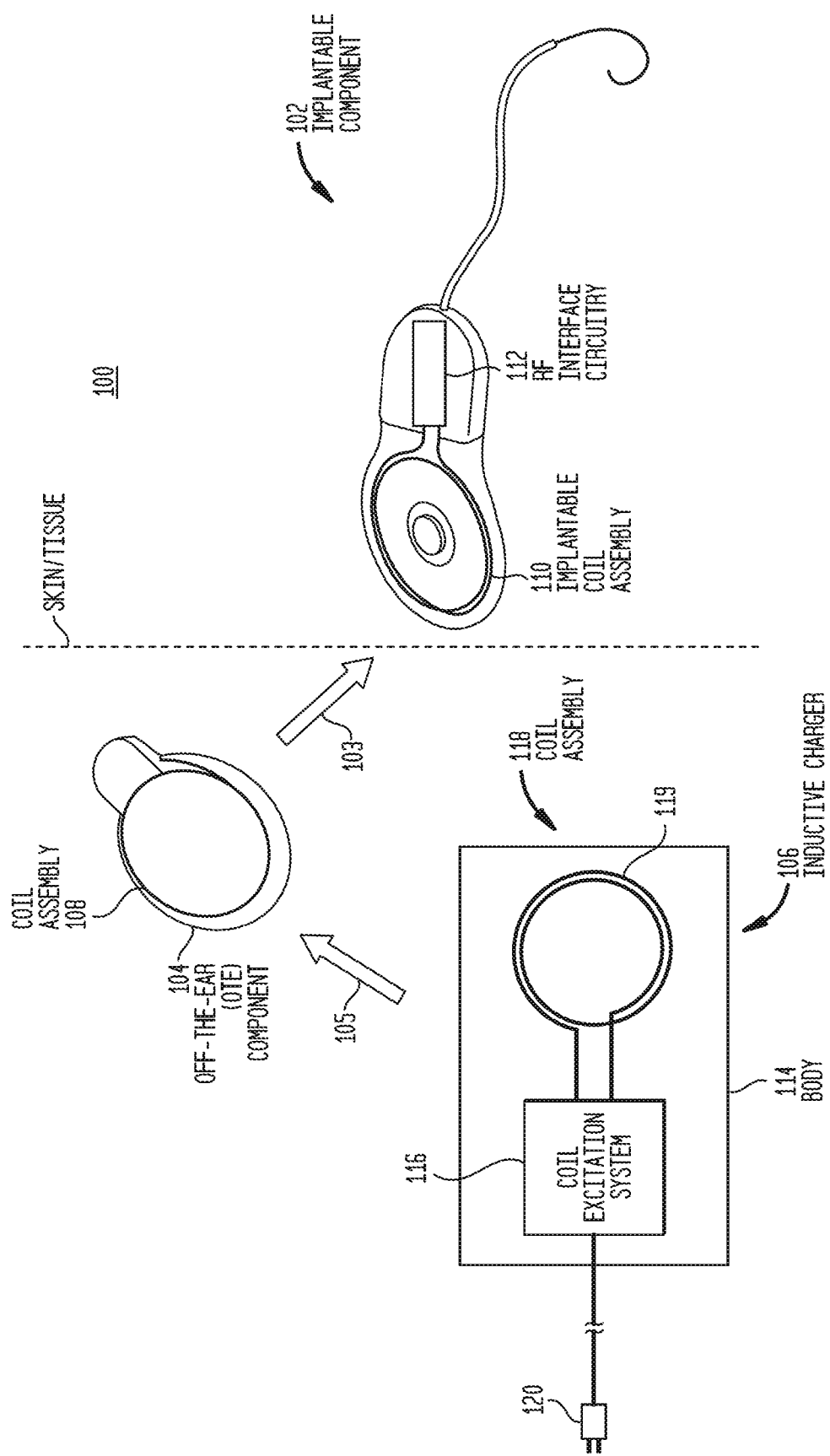

MEDICAL DEVICE COMPONENT WITH DUAL-BAND COIL ASSEMBLY

BACKGROUND

Field of the Invention

The present invention relates generally to external components of implantable medical device systems.

Related Art

Medical device systems having one or more implantable components, generally referred to herein as implantable medical device systems, have provided a wide range of therapeutic benefits to recipients over recent decades. In particular, partially or fully-implantable medical device systems such as hearing prosthesis systems (e.g., systems that include bone conduction devices, mechanical stimulators, cochlear implants, etc.), implantable pacemakers, defibrillators, functional electrical stimulation systems, etc., have been successful in performing lifesaving and/or lifestyle enhancement functions for a number of years.

The types of implantable medical device systems and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device system.

SUMMARY

In one aspect a method is provided. The method comprises: electrically connecting first and second coil segments of a coil assembly in a first electrically connected arrangement, wherein the coil assembly is positioned in an external component of an implantable medical device system; receiving, via the coil assembly in the first electrically connected arrangement, charging signals sent by an inductive charger at a first frequency; switching the coil assembly from the first electrically connected arrangement to a second electrically connected arrangement; and sending, via the coil assembly in the second electrically connected arrangement, transcutaneous signals from the external component to an implantable component at a second frequency, wherein the second electrically connected arrangement is different from the first electrically connected arrangement.

In another aspect an external component of an implantable medical device system is provided. The external component comprises: a coil assembly comprising a first coil segment and a second coil segment; a coil driver; a rechargeable battery; a battery manager; and at least one coil switch configured to, in response to receipt of low frequency charging signals at the coil assembly, automatically close so as to connect the first and second coil segments in series to provide the received charging signals to the battery charging circuit for use in recharging the rechargeable battery.

In another aspect, an external component of an implantable medical device system is provided. The external component comprises: a coil assembly comprising a first coil segment, a second coil segment, and a detection coil segment; a charger detection circuit configured to detect the presence of signals below a first frequency at the detection coil; and at least one controllable switch configured to close when the charger detection circuit detects the presence of signals below the first frequency at the detection coil so as to connect the first and second coil segments in a first electrically connected arrangement, wherein the at least one controllable switch is configured to be default open when the charger detection circuit does not detect the presence of signals below the first frequency at the detection coil such that so the first and second coil segments are connected in a second electrically connected arrangement.

BRIEF DESCRIPTION OF THE DRAWINGS

Embodiments of the present invention are described herein in conjunction with the accompanying drawings, in which:

FIG. 1 is a block diagram illustrating a cochlear implant system, in accordance with certain embodiments presented herein;

DETAILED DESCRIPTION

Figure 2A:
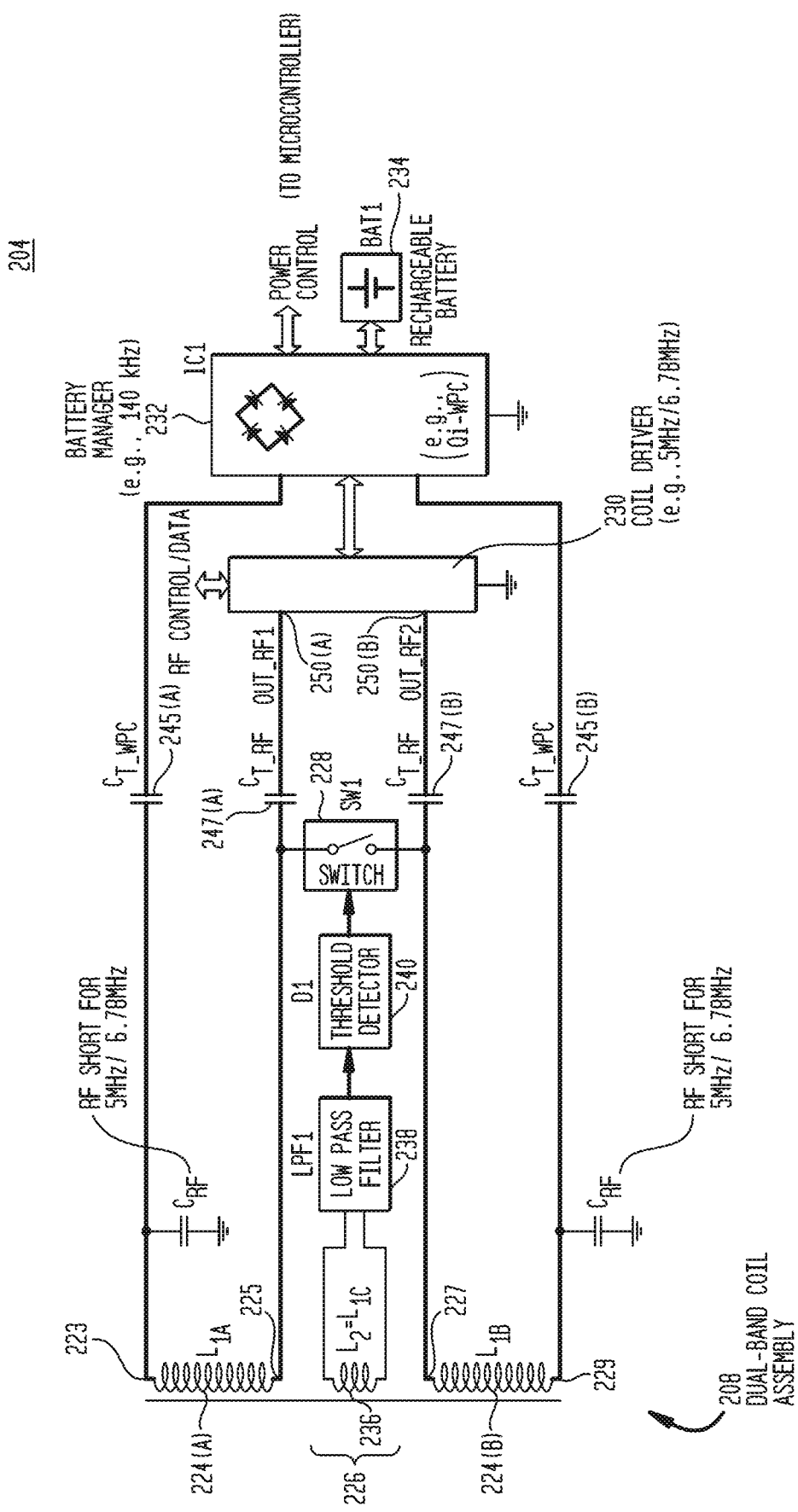
FIG. 2A is a simplified schematic diagram illustrating a medical device component with a dual-band coil assembly, in accordance with certain embodiments of the external component presented herein.

Implantable medical device systems include one or more components that are temporarily or permanently implanted within the body of a recipient. It is common for implantable medical device systems to also include, or operate in conjunction with, one or more external components/devices. In general, an external component provides functionality (e.g., processing capabilities, battery charging, etc.) that ensures proper operation of the associated implantable component(s). As a result, the external component transcutaneously communicates with (e.g., wirelessly transmits data to, wirelessly receives data from, and/or wirelessly provides power to) an associated implantable component. In certain arrangements, the external component includes a rechargeable battery that needs to be wireless recharged via power received from an inductive charger.

In conventional external components, an external component with a rechargeable battery includes two separate inductive coil assemblies, one for receiving charging signals (power) from an inductive charger and one for bi-directional transcutaneous communication with an implantable component (e.g., providing power, and potentially data to, the implantable component and/or receiving data from the implantable component). In these conventional arrangements, the two coil assemblies are generally oriented in different planes and/or occupy different areas of the external component. Increasingly, there is a desire to make medical device components, such as external components of implantable medical device systems, as small as possible (e.g., for aesthetic reasons, safety reasons, etc.). However, the need for two physically separate inductive coil assemblies, as in conventional components, inherently limits how small an external component can be made.

As such, presented herein are techniques that provide an external component with the ability to use a single inductive coil assembly to both receive charging signals from an inductive charger as well as for bi-directional transcutaneous communication with an implantable component. In particular, an external component comprises a coil assembly comprising a first coil segment and a second coil segment. The first and second coil segments have a first electrically connected arrangement that is used to receive charging signals, and a second electrically connected arrangement that is used for the bi-directional transcutaneous communication.

There are a number of different types of implantable medical device systems in which embodiments presented herein may be implemented. However, merely for ease of illustration, the techniques presented herein are primarily described with reference to one type of implantable medical device system, namely a cochlear implant system. It is to be appreciated that the techniques presented herein may be used in any other partially or fully implantable medical device system now known or later developed, including other auditory prosthesis systems, such as systems that include auditory brainstem stimulators, electro-acoustic hearing prostheses, middle ear prostheses, direct cochlear stimulators, bimodal hearing prostheses, etc. and/or other types of medical device systems, such as visual prosthesis systems, pain relief implants, pacemakers, etc.

FIG. 1 is block diagram of an exemplary cochlear implant system 100 in which embodiments presented herein are implemented. The cochlear implant system 100 comprises an implantable component 102 configured to be implanted under the skin/tissue of a recipient, an external component 104, and inductive charger 106.

In the example of FIG. 1, the external component 104 is an external device in the shape of a button configured to be worn "off-the-ear" of a recipient. As such, the specific external component 104 is also sometimes referred to as an off-the-ear (OTE) component or button. However, the external component 104 could alternatively be a behind-the-ear (BTE) component, in-the-ear (ITE) component, etc., which is configured to transfer power, and potentially data, to the implantable component 102.

The implantable component 102 comprises, among other elements, an implantable inductive coil assembly (implantable coil assembly) 110, a magnet (not shown in FIG. 1) positioned proximate to the implantable coil assembly 110, and radio-frequency (RF) interface circuitry 112, which enable the implantable component 102 to wirelessly communicate with OTE component 104. It is to be appreciated that implantable component 102 would include other components, such as a stimulator unit, electrode assembly, etc., that, for ease of illustration, have been omitted from FIG. 1.

The inductive charger 106 may comprise, for example, a charging mat, charging pad, charging base, base station, etc. that is configured to use an electromagnetic field to transfer energy to the external component 104 through electromagnetic induction (i.e., through an inductive coupling with the external component 104). To this end, the inductive charger 106 comprises a body 114 in which a coil excitation system 116 and one or more coil assemblies 118 are positioned. The one or more coil assemblies 118 are formed by a plurality of "loops" or "coils" 119 of wire, where the plurality of loops are sometimes collectively referred as a "wire-loop bundle." The inductive charger 106 also comprises an electrical connection 120 to a power source. In one example, the electrical connection includes a galvanic isolation element or a transformer (not shown in FIG. 1) to insulate the power source from the electronics of the inductive charger 106. The electrical connection 120 may also include a 12V DC adapter (not shown in FIG. 1).

In general, the coil excitation system 116 comprises one or more elements (e.g., a waveform generator, one or more amplifiers, tuning capacitors, etc.) that are used to drive the coil assembly 118 with an alternating current signal so that the coil assembly will emit a corresponding magnetic field. That is, when driven by the coil excitation system 116, the wire coils 119 hold varying electrical currents that generate/emit magnetic fields that, as described further below, can be used to inductively charge the external component 104. In certain examples, the coil excitation system 116 and coil assembly 118 are configured to operate in accordance with the Qi open interface standard defining wireless power transfer using inductive charging over distances of up to 4 cm (1.6 inches), developed by the Wireless Power Consortium.

The OTE component 104 includes, among other elements, a coil assembly 108, a magnet (not shown in FIG. 1), and a rechargeable battery (also not shown in FIG. 1). The OTE component 104 is configured to be recharged via power received from the inductive charger 106 (via inductive coupling of coil assemblies 108 and 118). The OTE component 104 is also configured to send power, and potentially data, to the implantable component 102 (via inductive coupling of coil assemblies 108 and 110).

That is, the OTE component 104 is configured for wireless communication with the implantable component 102, and for wireless communication with the inductive charger 106. In FIG. 1, the wireless communication between OTE component 104 and implantable component 102, sometimes referred to herein as a bi-directional "transcutaneous link," is represented by arrow 103. Similarly, the wireless communication between OTE component 104 and inductive charger 106, sometimes referred to herein as a "charging link," is represented by arrow 105. As described further below, the single coil assembly 108 of OTE component 104 is used for receiving charging signals (power) from the inductive charger 106 via the charging link 105, as well as for transferring power to, and potentially transferring data and/or receiving data from, the implantable component 102 via transcutaneous link 103.

In practice, the transcutaneous link 103 and the charging link 105 operate at different frequencies, where lower frequencies are typically used for the charging link and higher frequencies are used for the transcutaneous link. For example, transcutaneous link 103 may operate at approximately 5 Megahertz (MHz), at approximately 6.78 MHz, at approximately 13.56 MHz, at approximately 27.12 MHz, etc., while the charging link 105 may operate at approximately less than 400 kilohertz (kHz), as at approximately 140 kHz, at approximately 100 kHz, less than 100 kHz, etc. In accordance with embodiments presented herein, the coil assembly 108 of the OTE component 104 is configured to selectively operate at both the transcutaneous link frequency and the charging link frequency (i.e., operate in one mode, e.g., 140 kHz Qi WPC, for accepting wireless power charging signals and in another mode operate at, e.g., 5 MHz, 6.8 MHz, etc. for delivering power to the implant). As such, the coil assembly 108 of the OTE component 104 is sometimes referred to herein as a dual-band wireless power transfer coil assembly or, more simply, as a "dual-band coil assembly."

Although FIG. 1 illustrates both the transcutaneous link 103 and the charging link 105, it is to be appreciated that these two links would be operative at different times. In particular, the transcutaneous link 103 would only be activate and operational when the OTE component 104 is positioned in close proximity to the implantable component 102, such as when the OTE component 104 is worn on the head of the recipient. The magnets in the OTE component 104 and the implantable component 102 may cooperate to retain the OTE component 104 on the recipient's head and to align the coil assemblies 108 and 110, thereby facilitating the inductive coupling and formation of the transcutaneous link 103.

Conversely, the charging link 105 would only be activate and operational when the OTE component 104 is positioned in close proximity to the inductive charger 106. For instance, a recipient may remove the OTE component 104 from his/her head and place the OTE component 104 on top of the inductive charger 106 so that the coil assemblies 108 and 118 are in close proximity to one another.

FIG. 2A is a simplified schematic diagram illustrating further details of an example external component, such as OTE component 104, that is configured in accordance with certain embodiments presented herein. For ease of description, the external component of FIG. 2A is referred to as OTE component 204.

OTE component 204 comprises a coil assembly 208, sometimes referred to as a "dual-band coil assembly." In the example of FIG. 2A, the dual-band coil assembly 208 comprises a first coil section/segment 224(A), sometimes referred to herein as $L_{1A}$, and a second coil segment/section 224(B), sometimes referred to herein as $L_{1B}$. The first coil segment 224(A) has a first end 223, and a second end 225. The second coil segment 224(B) has a first end 227, and a second end 229.

The OTE component 204 also comprises a charger detection circuit 226, a coil switch 228, a coil driver 230 (e.g., a 5 MHz, 6.78 Mhz, etc. Class-D/E driver), a battery manager/charging circuit 232 (e.g., Qi-WPC manager), and a rechargeable battery 234. In the example of FIG. 2A, the charger detection circuit 226 comprises a sniffer or detection coil segment 236, sometimes referred to herein as $L_2$ or $L_{1C}$, a low pass filter 238, and a threshold detector 240.

As noted above, dual-band coil assemblies in accordance with embodiments presented herein, such as dual-band coil assembly 208, is operable in first and second modes. In the first mode, sometimes referred to herein as the "battery charging mode," the first coil segment 224(A) and the second coil segment 224(B) have a first electrically connected arrangement that enables the dual-band coil assembly 208 to receive charging signals from an inductive charger (e.g., inductive charger 106), where the charging signals are transmitted/sent at a first frequency. In the second mode, sometimes referred to as the "transcutaneous transfer mode," the first coil segment 224(A) and the second coil segment 224(B) have a second electrically connected arrangement that enables the of the dual-band coil assembly 208 to send/transmit transcutaneous signals (e.g., power and/or data) to an implantable component (e.g. implantable component 102). The transcutaneous signals are transmitted/sent at a second frequency that is different from the first frequency, and the second electrically connected arrangement of the coil segments 224(A) and 224(B) is different from the first electrically connected arrangement of the coil segments 224(A) and 224(B). Each of the battery charging mode and the transcutaneous transfer mode of the dual-band coil assembly 208 are described further below.

More specifically, in the battery charging mode, the coil segments 224(A) and 224(B) are in series resonance to load the battery at a lower frequency (e.g., battery charging at 140 kHz (WPC), where turns $L_{1A}$ and 4 turns $L_{1B}$ are closely coupled to the Qi coil assembly of the inductive charger). During the battery charging mode, coil switch 228 is closed so as to bypass (short) the coil driver 230 to directly connect coil segments 224(A) and 224(B) in series. More specifically, coil switch 228 connects the second end 225 of coil segment 224(A) to first end 227 of second coil segment 224(B).

Figure 2B:
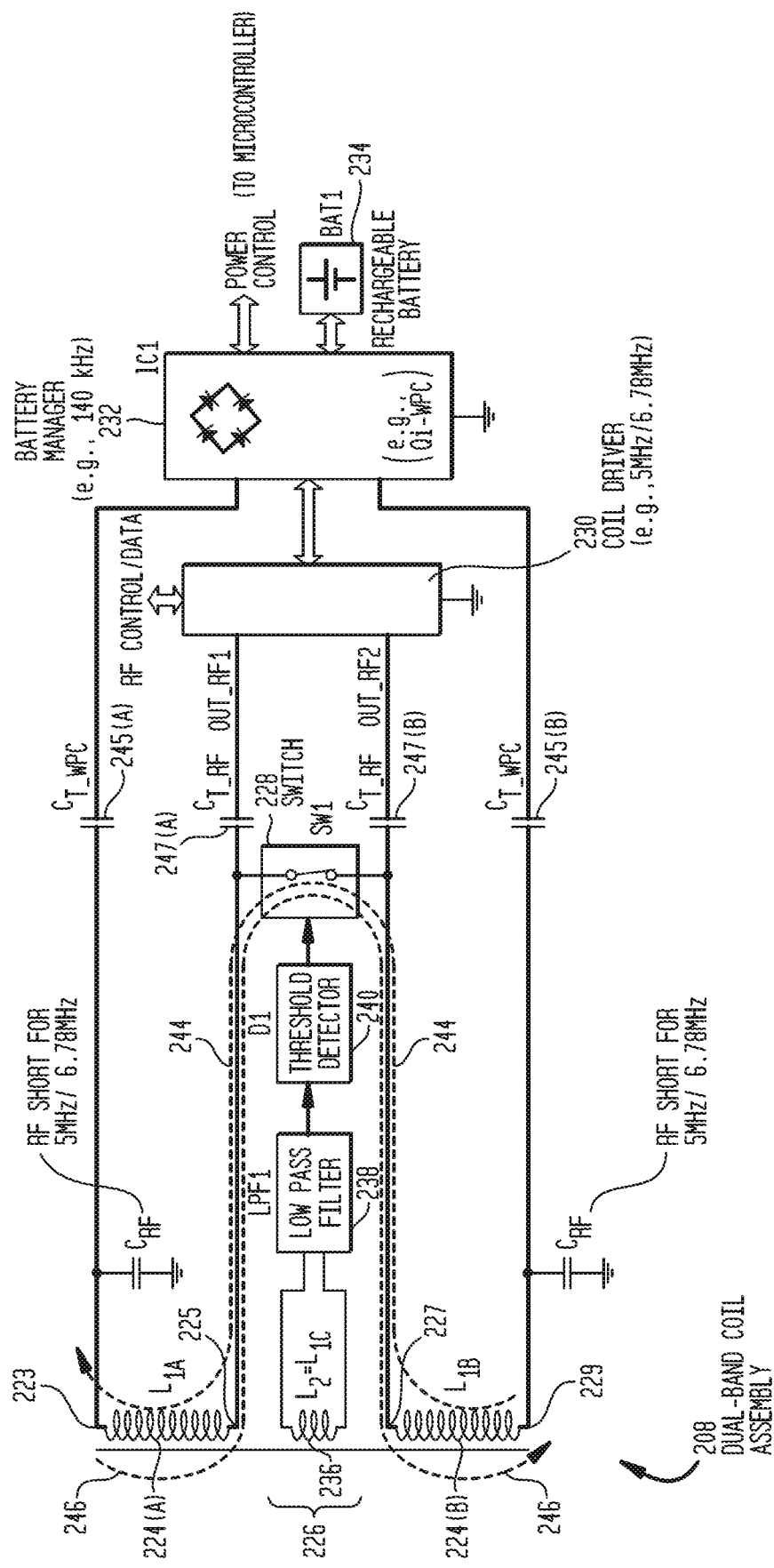
FIG. 2B is a simplified schematic diagram illustrating current flow in the medical device component of FIG. 2A during a first mode, in accordance with certain embodiments of the external component presented herein.

FIG. 2B is a schematic diagram of the OTE component 204 illustrating the flow of current through dual-band coil assembly 208 during the battery charging mode. In particular, arrow 244 illustrates the flow of current during a first phase, while arrow 246 illustrates the flow of current during a second phase (i.e., alternating current induced via the inductive charger). As shown by arrows 244 and 246, in each of these two current phases, the current passes serially between the coil segments 224(A) and 224(B) through (via) coil switch 228. Therefore, FIG. 2B illustrates that, during the battery charging mode, the coil switch 228 is closed so as to directly connect dual-band coil assembly 208 (i.e., the turns of $L_{1A}$ and the turns $L_{1B}$) to the battery manager 232, utilizing mainly a series resonance circuit (i.e., with the $C_{T\_WPC}$ capacitors 245(A) and 245(B)).

Returning to FIG. 2A, the battery charging mode is activated whenever the dual-band coil assembly 208 is inductively coupled to the coil assembly of an inductive charger. The inductive coupling of the dual-band coil assembly 208 is inductively coupled to the coil assembly of an inductive charger is detected by the charger detection circuit 226. More specifically, when a user places the OTE component 204 on top of an inductive charger, the detection coil segment 236 will be exposed to the electromagnetic field generated by the inductive charger. As such, current signals will be induced in the detection coil segment 236 and these current signals are provided to low pass filter 238.

As noted above, the charging signals (electromagnetic field generated by the inductive charger) are associated with lower frequencies (e.g., 140 kHz), while the transcutaneous signals (electromagnetic fields generated by the OTE component 204 and/or an implantable component) are associated with higher frequencies (e.g., 5 Mhz, 6.78 Mhz, etc.). Therefore, the current signals induced in the detection coil segment 236 by the inductive charger will have a corresponding lower frequency (e.g., 140 kHz). The low pass filter 238 has an upper cut-off frequency that is sufficiently high so as to enable these lower frequency current signals to pass there through, but also which is low enough to block any current signals induced in the detection coil segment 236 as result of transcutaneous communication (e.g., block 5 Mhz, 6.78 Mhz, etc. signals induced by electromagnetic fields generated by the OTE component 204 and/or an implantable component).

As noted, FIG. 2A also illustrates that the charger detection circuit 226 includes the threshold detector 240. If current signals pass through the low pass filter 238, the threshold detector 240 determines whether they should be provided to the coil switch 228. That is, the threshold detector 240 verifies/determines that the current signals are induced by an inductive charger, and not by the OTE component 204 itself and/or an implantable component. The threshold detector 240 may make this determination, for example, based on the amplitude level of the voltage or current, but also the frequency, or other attributes of the present signals (e.g., ensure the frequency is below a predetermined threshold). It is to be appreciated that, if the low pass filter 238 was sufficiently robust, the threshold detector 240 could be omitted in certain embodiments.

Once the induced signals at detection coil segment 236 pass through the low pass filter 238 and the threshold detector 240, the induced signals are rectified to direct current (DC) (e.g., at threshold detector 240 or at a separate rectifier) and provided to the coil switch 228. The DC current generated by the induced signals causes the coil switch 228 to close and, as noted above, connect coil segments 224(A) and 224(B) together in series. As such, the coil switch 228 is powered by current drawn from the inductive charger via detection coil segment 236. In this way, even if the battery 234 is empty, the coil switch 228 can still close so as to directly connect dual-band coil assembly 208 (i.e., the turns of $L_{1A}$ and the turns $L_{1B}$) to the battery manager 232, utilizing mainly a series resonance circuit (i.e., with the $C_{T\_WPC}$ capacitors 245(A) and 245(B)). Moreover, as noted above, coil switch 228 is only closed when the OTE component 204 is placed on the inductive charger and not when the detection coil segment 236 are exposed to electromagnetic fields generated by the OTE component 204 itself and/or an implantable component.

Stated differently, the coil switch 228 is driven by a third (floating) coil (detection coil segment 236) that extracts the electromagnetic field (e.g., 140 kHz field) from the inductive charger. Removing the OTE component 204 from the inductive charger automatically opens the coil switch 228. The coil switch 228 may comprise, for example, one or more Metal Oxide Semiconductor Field Effect Transistors (MOSFETs), one or more bipolar transistors, microelectromechanical system (MEMS) coil switch, an optocoupler, miniature electro-mechanic coil switch, etc.

Returning to the example of FIG. 2A, as noted above, the detection coil segment 236 are used to detect the presence of the inductive charger and to obtain signals that are used to close the coil switch 228. The detection coil segment 236 is galvanically insulated from coil segments 224(A) and 224(B) (i.e., electrically floating relative to segments 224(A) and 224(B)), although coil segments 224(A), 224(B) and detection coil segment 236 may be part of the same coil geometry and are located proximate to one another (e.g., all are well magnetically coupled and at the same surface of the OTE component 204).

In certain embodiments, the detection coil segment 236 also functions as a dampening coil used during the transcutaneous communication with an implantable component. In such embodiments, the detection coil segment 236 is used, during transcutaneous communication to optimize the integrity of the near-field communication link over a large range of recipient skin flap thicknesses (i.e., used to lower the "Q" during data/power transfer with an implantable component).

As noted, in addition to the battery charging mode described above, the dual-band coil assembly 208 is also operable in a transcutaneous transfer mode when the dual-band coil assembly 208 is closely coupled to an implantable coil (e.g., coil 110 of FIG. 1). As such, during the transcutaneous transfer mode, the first coil segment 224(A) and the second coil segment 224(B) have a second electrically connected arrangement that enables the of the dual-band coil assembly 208 to send/transmit transcutaneous signals (e.g., power and/or data) to an implantable component (e.g. implantable component 102). In the transcutaneous transfer mode, coil segments 224(A) and 224(B) are oppositely coupled to one another seen from the coil driver 230 (e.g., coupled together at a center point via the coil driver). More specifically, during the transcutaneous transfer mode coil switch 228 is open such that the second end 225 of coil segment 224(A), as well as the first end 227 of second coil segment 224(B), are each electrically connected to outputs 250(A) and 250(B), respectively, of coil driver 230 (differential output driver).

Figure 2C:
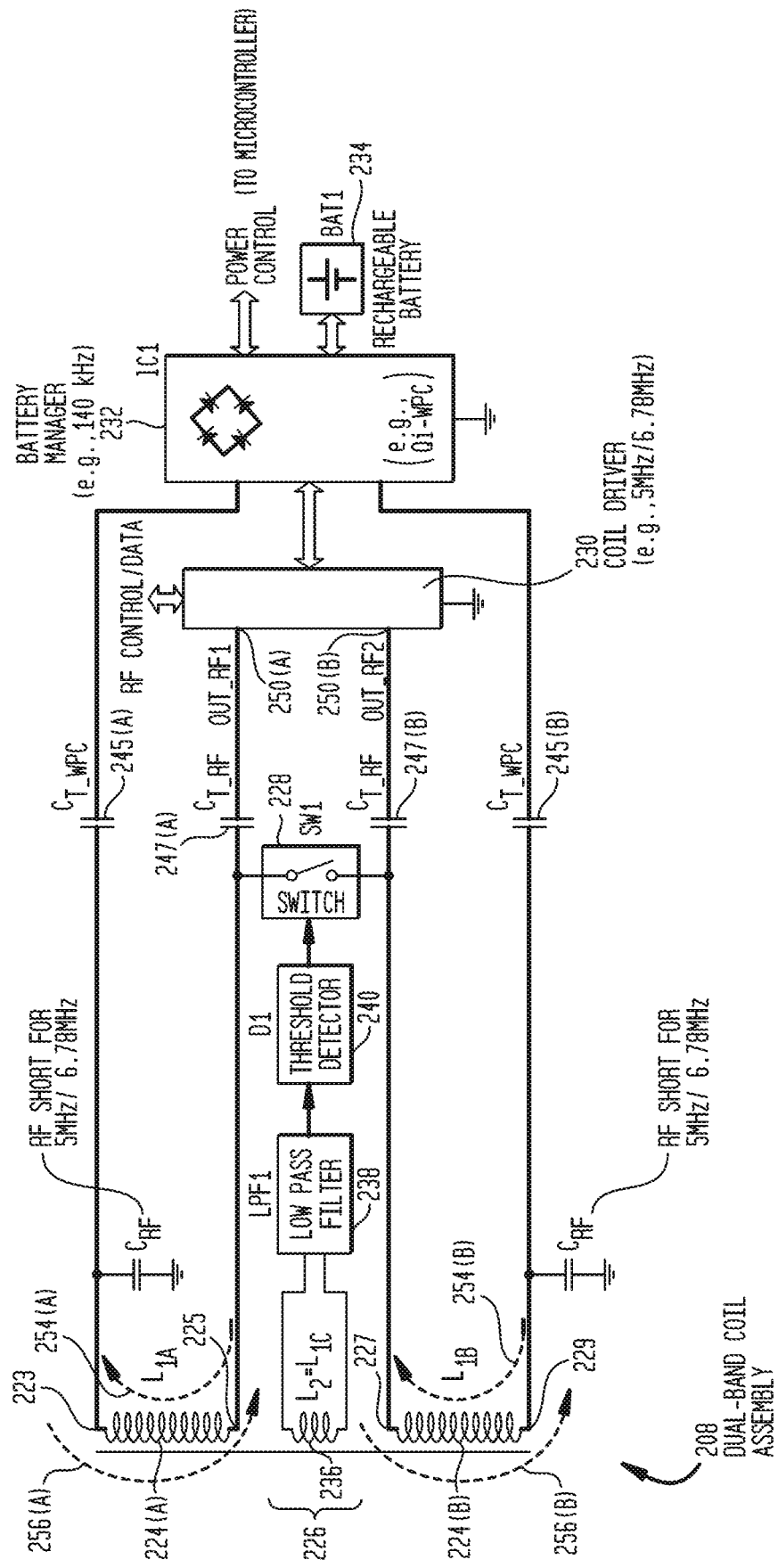
FIG. 2C is a simplified schematic diagram illustrating current flow in the medical device component of FIG. 2A during a second mode, in accordance with certain embodiments of the external component presented herein.

FIG. 2C is a schematic diagram of the OTE component 204 illustrating the flow of current through dual-band coil assembly 208 during the transcutaneous transfer mode. In particular, arrows 254(A) and 254(B) illustrate the flow of current through coil segments 224(A) and 224(B), respectively, during a first phase, while arrows 256(A) and 256(B) illustrate the flow of current through coil segments 224(A) and 224(B), respectively, during a second phase (i.e., alternating current induced via the inductive charger). As shown by arrows 254(A) and 254(B) and arrows 256(A) and 256(B), in each of the two current phases, the two coil segments 224(A) and 224(B) are differentially driven so that, at any given time instance, the current pass through both of the coil segments in the same sense/direction, but with opposite phases (i.e., at a given time instant signals through $L_{1A}$ and $L_{1B}$ are opposite in phase, but in the same direction so as not to cancel one another). Stated differently, at a given time instance during the first phase, output 250(A) of coil driver 230 sources current, while output 250(B) of coil driver 230 sinks current. Conversely, at a given time instance during the second phase, output 250(A) of coil driver 230 sinks current, while output 250(B) of coil driver 230 sources current. During the transcutaneous transfer mode, coil segments 224(A) and 224(B) are in resonance with capacitors 247(A) and capacitors 247(B) (i.e., $C_{T-RF}$).

Returning to FIG. 2A, the transcutaneous transfer mode is activated in the presence of an implantable component (i.e., when dual-band coil assembly 208 is inductively coupled to an implantable coil) and once the battery 234 is sufficiently charged. The inductive coupling to an implantable component does not need to be detected since the coil switch 228 is default open. That is, when a user removes the OTE component 204 from the top of an inductive charger, the coil switch 228 opens to connect remove the bypass of coil driver 230.

More specifically, as noted above, the charging signals (electromagnetic field generated by the inductive charger) are associated with lower frequencies (e.g., 140 kHz), while the transcutaneous signals (electromagnetic fields generated by the OTE component 204 and/or an implantable component) are associated with higher frequencies (e.g., 5 Mhz, 6.78 Mhz, etc.). Therefore, any current or voltage signals induced in the detection coil segment 236 during transcutaneous transfer will be above the upper cut-off frequency of low pass filter 238. Accordingly, the signal will be blocked by the low pass filter 238 and/or the threshold detector 240, and the coil switch 228 will unpowered (open) (i.e., a low-pass filter 228 prevents that fields at 5 MHz or 6.78 MHz from closing the coil switch 228 and the 5 MHz or 6.78 MHz coil driver 230 becomes active).

In summary, FIGS. 2A, 2B, and 2C illustrate an example arrangement in which a single coil assembly 208 is able to operate in two modes, one mode that receives battery charging signals and provides recharging power to the battery 234 of the OTE component 204 and another mode that provides power (and potentially data) to an implantable component, with bidirectional operation. In accordance with the above embodiments, to receive the battery charging signals at a first frequency, the coil switch 228 is closed to connect the first and second coil segments 224(A) and 224(B) in a first electrically connected arrangement. To transfer transcutaneous power and/or data signals to the implantable component, the coil switch 228 is opened so that the first and second coil segments 224(A) and 224(B) have a second electrically connected arrangement in which the coils are only differentially connected through the coil driver 230.

As noted, the switch 228 is powered via signals drawn from the inductive charger (e.g., signals received at $L_{1C}$, low pass filtered (LPF), rectified to DC current and applied to the switch). The use the low pass filter 238 blocks 5 MHz or 6.78 MHz, etc. signals so that the switch 228 is always open when the dual-band coil assembly 208 is not coupled to the inductive charger (i.e., self-powered insulated/floating switch connects the two coil segments together only during battery charging).

Figure 3:
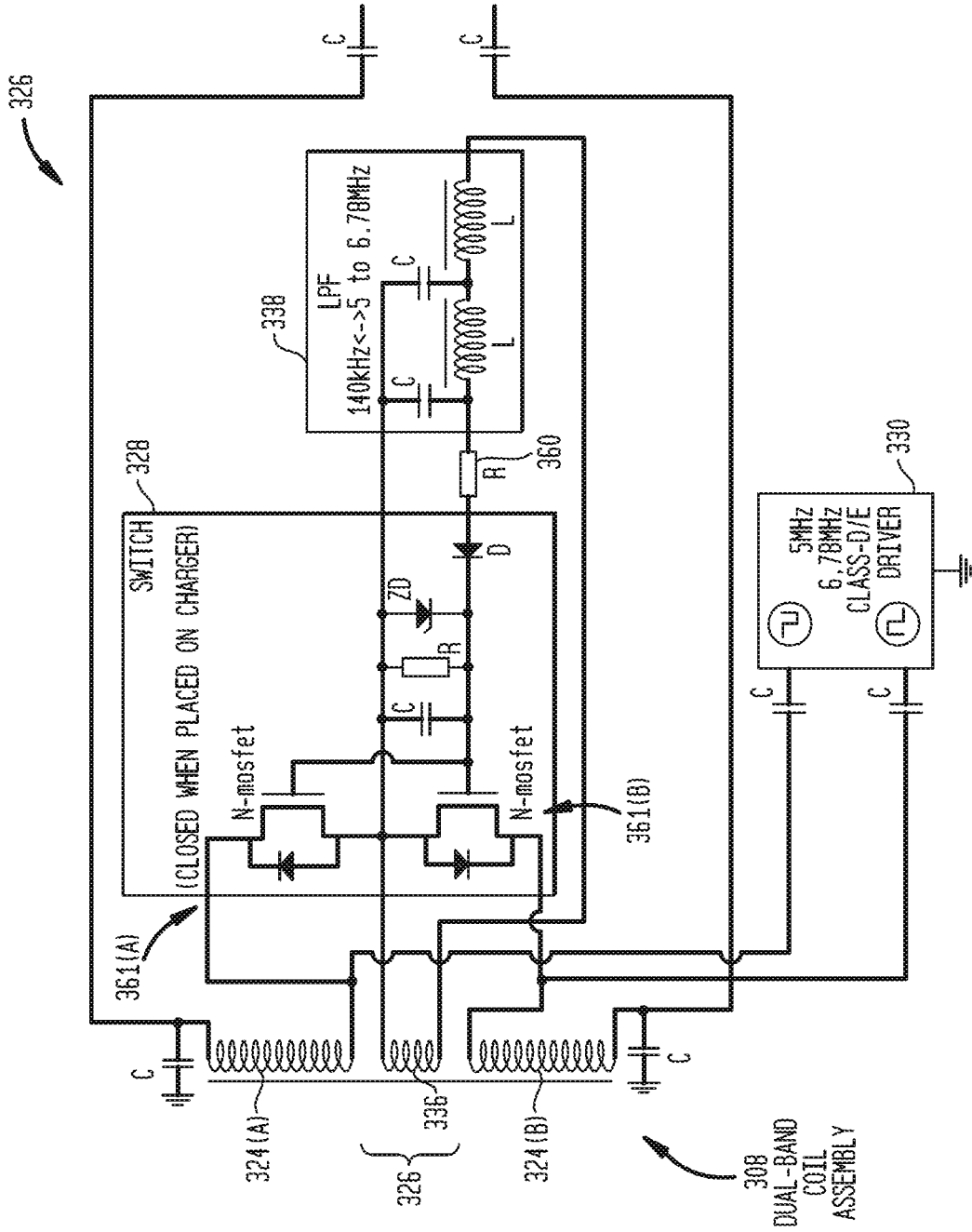
FIG. 3 is a simplified schematic diagram illustrating further details of a coil switch, in accordance with certain embodiments of the external component presented herein.

As noted above, external components in accordance with embodiments presented herein may include a number of different types of coil switches to selectively connect two coil segments in series for receipt of charging signals. For example, coil switches in accordance with embodiments presented herein may be formed by one or more Metal Oxide Semiconductor Field Effect Transistors (MOSFETs), one or more bipolar transistors, microelectromechanical system (MEMS) coil switch, an optocoupler, miniature electro-mechanic coil switch, etc. FIG. 3 is schematic diagram illustrating further details of one example coil switch, in accordance with embodiments presented herein.

More specifically, FIG. 3 illustrates a portion of an external component 304, including a dual-band coil assembly 308, a charger detection circuit 326, a coil switch 328, and a coil driver 330 (e.g., a 5 MHz, 6.78 Mhz, etc. Class-D/E driver). Omitted from FIG. 3 are a number of elements, such as the battery manager (e.g., Qi-WPC manager), rechargeable battery, etc. described elsewhere herein. The dual-band coil assembly 308 comprises a first coil section/segment 324(A) and a second coil segment/section 324(B).

In the example of FIG. 3, the charger detection circuit 326 comprises a sniffer or detection coil segment 336, a low pass filter 338, and a rectifier 360. Additionally, the specific switch 328 of FIG. 3 is formed by a two N-type MOSFETS 361(A) and 361(B). As described above, when the dual-band coil assembly 308 is inductively coupled to an inductive charger, the switch 328 closes to connect coil segments 324(A) and 324(B) in series and, accordingly, short/shunt coil driver 330 (i.e., the two N-type MOSFETS 361(A) and 361(B) cooperate to directly electrically connect the two coil segments 324(A) and 324(B) together). When the dual-band coil assembly 308 is not inductively coupled to an inductive charger, the switch 328 is default open so as to remove the shunt around coil driver 330 (i.e., the two N-type MOSFETS 361(A) and 361(B) cooperate to electrically separate the two coil segments 324(A) and 324(B), except for an connection via the coil driver).

Figure 4:
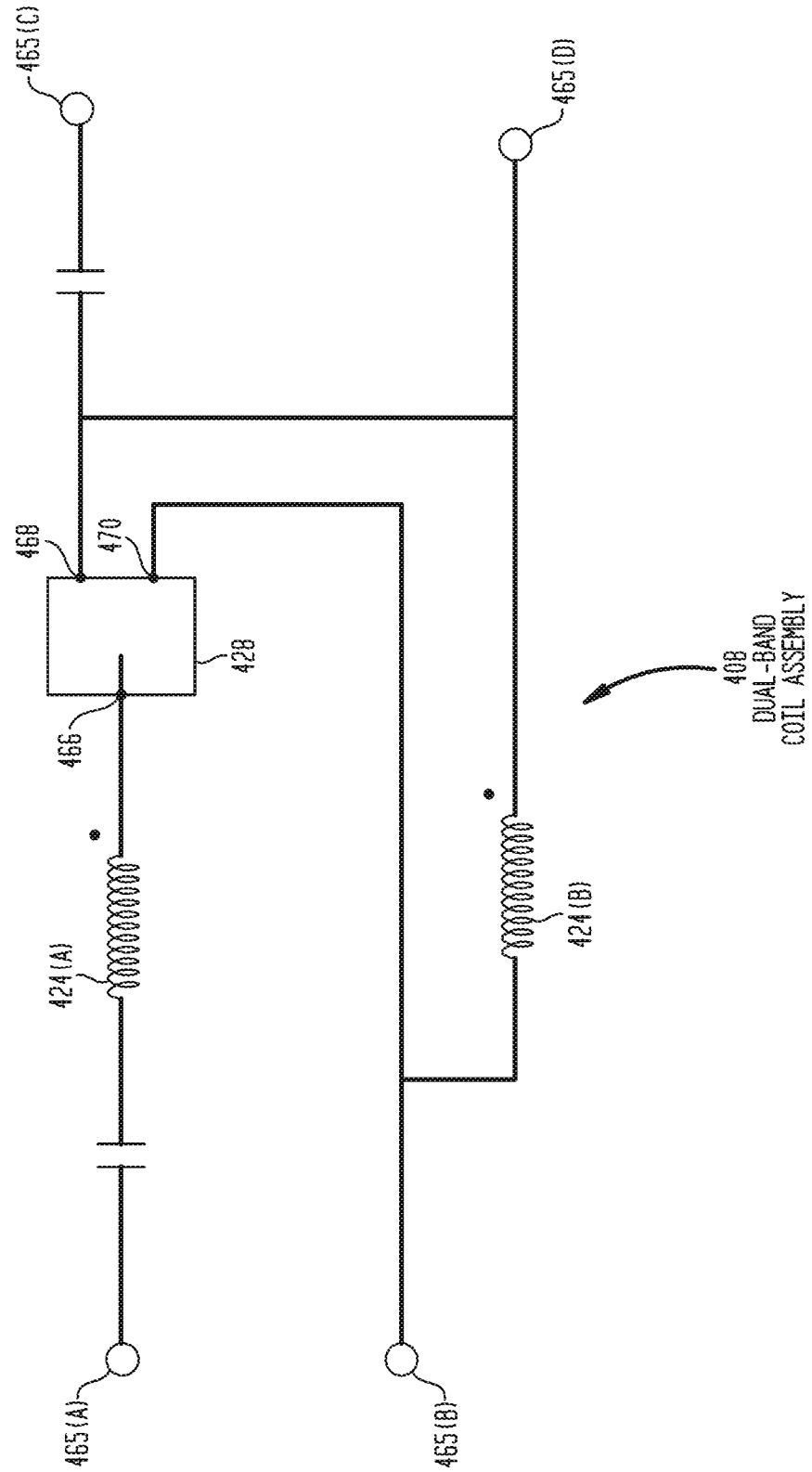
FIG. 4 is a simplified schematic diagram illustrating a medical device component with a dual-band coil assembly, in accordance with certain embodiments of the external component presented herein.

As noted above, FIGS. 2A, 2B, 2C, and 3 generally illustrate arrangements in which, during the battery charging mode, the coil segments are connected in series, while during the transcutaneous transfer mode, the coil segments are differentially connected to a coil driver. FIG. 4 illustrates an alternative arrangement in which during the battery charging mode, the coil segments are connected in series, while during the transcutaneous transfer mode, the coil segments are connected in parallel.

More specifically, FIG. 4 illustrates a portion of an external component 404, including a dual-band coil assembly 408, and a coil switch 428. Omitted from FIG. 4 are a number of elements, such as the coil driver, battery manager (e.g., Qi-WPC manager), rechargeable battery, etc. described elsewhere herein. The dual-band coil assembly 408 comprises a first coil section/segment 424(A) and a second coil segment/section 424(B).

In the example of FIG. 4, the coil switch 428 is a multiple position switch, comprising nodes 466, 468, and 470. During a battery charging mode, the switch 428 is activated to connect node 466 with node 470 and, accordingly, place coil segments 424(A) and 424(B) in series. In this operational mode, power is received via circuit nodes 465(A) and 465(D), while nodes 465(B) and 465(C) are open circuit. During a transcutaneous transfer mode, the switch 428 is activated to connect node 466 with node 468 and, accordingly, place coil segments 424(A) and 424(B) in parallel. In this operational mode, circuit nodes 465(A) and 465(B) are driven together in phase or simply electrically shorted and connected to the first side of the RF bridge, node 465(C) is a second side of an RF bridge, and node 465(D) is open circuit.

As noted, FIG. 4 illustrates the use of a multiple position coil switch 428. It is to be appreciated that, in alternative embodiments, the multiple position coil switch 428 could be replaced by a plurality of switches that selectively connect the coil segments 424(A) and 424(B) in series or in parallel.

In summary, FIG. 4 illustrates an arrangement in which the coil segments 424(A) and 424(B) can be switched between a low inductance configuration (parallel connection) and a high inductance configuration (series connection). The series connection of coil segments 424(A) and 424(B) is used when the dual-band coil assembly 408 is inductively coupled to a coil assembly of an inductive charger (e.g., for 140 kHz Qi communication). The parallel connection of coil segments 424(A) and 424(B) is used when the dual-band coil assembly 408 is inductively coupled to a coil assembly of an implantable component (e.g., for 5 Mhz, 6.78 Mhz, etc. communication).

Figure 5:
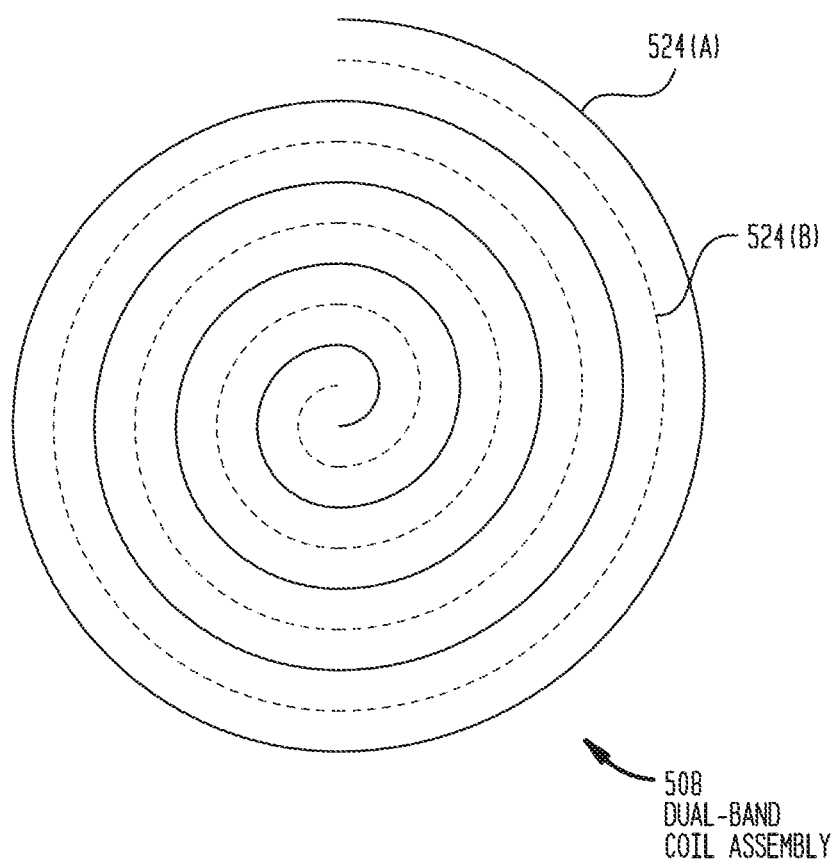
FIG. 5 is a simplified schematic diagram of a dual-band coil assembly, in accordance with certain embodiments of the external component presented herein.

FIG. 5 is a schematic view of one physical arrangement for two coil segments, such as coil segments 224(A) and 224(B), 324(A) and 324(B), 424(A) and 424(B), etc., in accordance with certain embodiments presented herein. More specifically, FIG. 5 illustrates two coil segments, referred to as coil segments 524(A) and 524(B), which are co-centric with one another to form one physical assembly (i.e., two adjacent windings) so as to be positioned at the same surface of an external component. The techniques described elsewhere herein may be used to selectively connect the coil segments 524(A) and 524(B) in first and second arrangements (e.g., (1) series connection or differential connection, (2) series connection or parallel connection, etc.)

Figure 6:
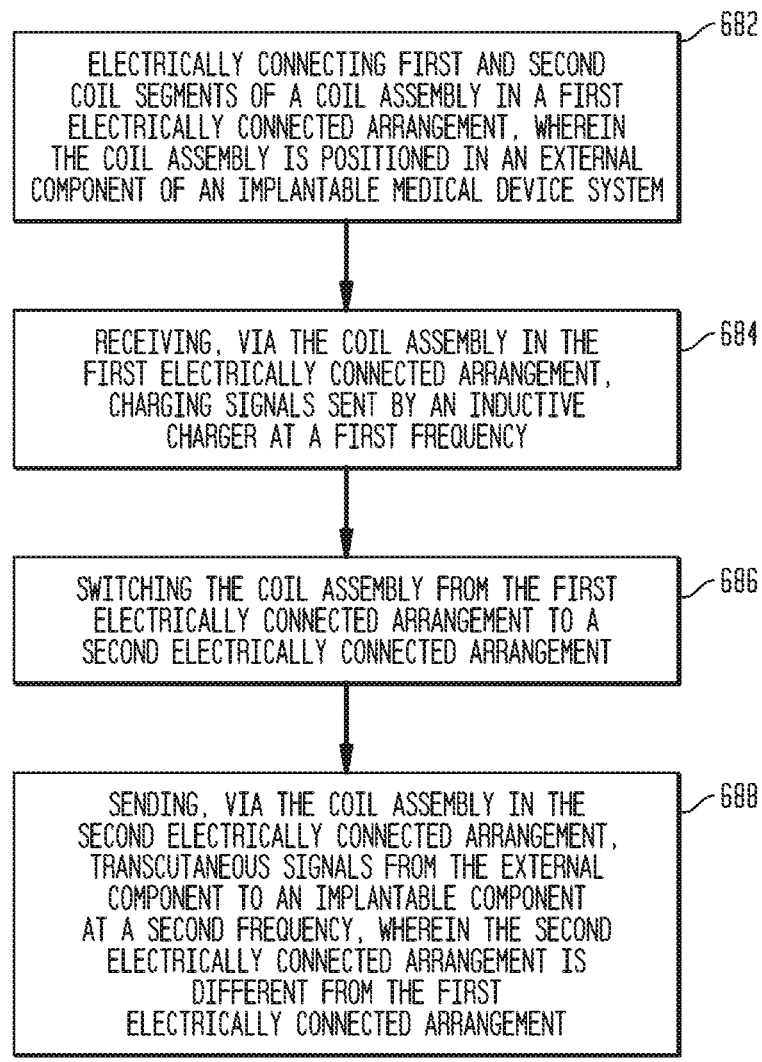
FIG. 6 is a flowchart of a method, in accordance with certain embodiments of the implantable medical device system presented herein.

FIG. 6 is a flowchart of a method 680 in accordance with certain embodiments presented herein. Method 680 begins at 682 where first and second coil segments of a coil assembly, which is positioned in an external component of an implantable medical device system, are electrically connected in a first electrically connected arrangement. At 684, charging signals sent by an inductive charger are received, via the coil assembly in the first electrically connected arrangement, at a first frequency. At 686, the coil assembly is switched from the first electrically connected arrangement to a second electrically connected arrangement. At 680, transcutaneous signals are sent, via the coil assembly in the second electrically connected arrangement, from the external component to an implantable component at a second frequency. The second electrically connected arrangement is different from the first electrically connected arrangement.

As noted above, conventional external components of medical device systems include two separate coil assemblies, where a first coil assembly is used to receive battery charging signals from an inductive charger and a second coil assembly is used for bi-directional transcutaneous communication within an implantable component. Additionally, the two coil assemblies are typically positioned at different areas/surfaces of the external. The need for two coil assemblies disposed at separate locations not only inherently increases the size of conventional components, but also requirements different physical orientations of the component for each of the two types of communications (e.g., the second coil assembly requires user to place the eternal upside down or at 90 degrees angle relative to the inductive charger). Presented herein are external components (e.g., OTE power buttons, OTE sound processors, BTE sound processors, etc.) of medical device systems in which a single coil assembly is used to both receive battery charging signals from an inductive charger and for bi-directional transcutaneous communication within an implantable component. The use of a single coil assembly reduces the size requirements for an external component, relative to conventional arrangements requirement two separate coil assemblies and enables the use of a single physical orientation for each of the two types of communications.

Embodiments presented herein have primarily been described with reference to cochlear implant systems, in particular, have generally been described with reference to one example arrangement of a cochlear implant system configured to implement the techniques presented. However, as noted elsewhere wherein, the techniques presented herein may also or alternatively be used with other types of cochlear implant systems and/or any other implantable medical device system now known or later developed. Example systems in which the techniques presented may be implemented include, but are not limited to, other auditory prosthesis systems (e.g., systems that include auditory brainstem stimulators, electro-acoustic hearing prostheses, middle ear prostheses, bone conduction devices, direct cochlear stimulators, bimodal hearing prostheses, etc.) and/or other types of medical device systems, such as spinal cord stimulators, deep brain stimulators, motor cortex stimulators, sacral nerve stimulators, pudendal nerve stimulators, vagus/vagal nerve stimulators, trigeminal nerve stimulators, retinal or other visual prosthesis/stimulators, occipital cortex implants, diaphragm (phrenic) pacers, pain relief stimulators, other neural or neuromuscular stimulators, etc. For example, FIG. 7 is a schematic diagram of one type of alternative medical device system, namely a pain relief system including a spinal cord stimulator, in which certain techniques presented herein may be implemented.

Figure 7:
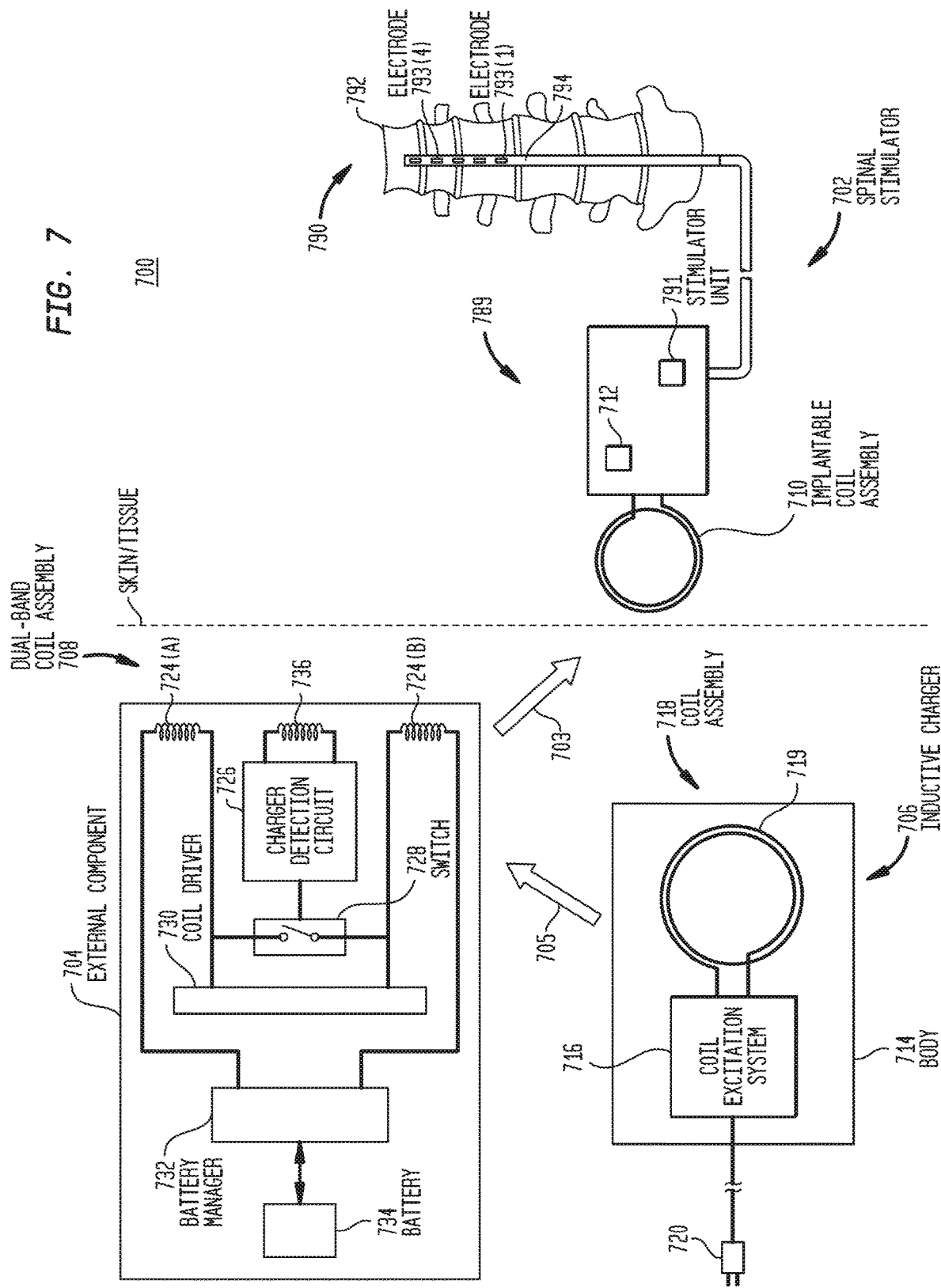
FIG. 7 is a schematic block diagram illustrating a spinal cord stimulator, in accordance with certain embodiments presented herein.

More specifically, the pain relief system 700 of FIG. 7 comprises an implantable component 702 configured to be implanted under the skin/tissue of a recipient, an external component 704, and inductive charger 706. The implantable component 702 is a spinal cord stimulator that comprises, among other elements, an implant body (main module) 789 and a stimulating assembly 790 implanted under the skin/tissue (tissue) of the recipient. The implant body 789 generally comprises, among other elements, an implantable coil assembly 710, a magnet (not shown in FIG. 7) positioned proximate to the implantable coil assembly 710, a stimulator unit 791, and radio-frequency (RF) interface circuitry 712, which enable the spinal cord stimulator 702 to wirelessly communicate with external component 704.

The stimulating assembly 790 is implanted in a recipient adjacent/proximate to the recipient's spinal cord 792 and comprises five (5) stimulation electrodes 793, referred to as stimulation electrodes 793(1)-793(5). The stimulation electrodes 793(1)-793(5) are disposed in an electrically-insulating body 794 and are electrically connected to the stimulator unit 791 via conductors (not shown) that extend through the electrically-insulating body 794.

Following implantation, the stimulator unit 791 is configured to generate stimulation signals for delivery to the spinal cord 792 via stimulation electrodes 793(1)-793(5). In FIG. 7, external component 704 provides power and/or data to the spinal cord stimulator 702 for use in generating the stimulation signals and/or powering components of the spinal cord stimulator. It is to be appreciated that spinal cord stimulator 702 would include other components that, for ease of illustration, have been omitted from FIG. 7.

The inductive charger 706 is similar to inductive charger 706 described above with reference to FIG. 1 and, as such, may be a charging mat, charging pad, charging base, base station, etc. that is configured to use an electromagnetic field to transfer energy to the external component 704 through electromagnetic induction (i.e., through an inductive coupling with the external component 704). To this end, the inductive charger 706 comprises a body 714 in which a coil excitation system 716 and one or more coil assemblies 718 are positioned. The one or more coil assemblies 718 are formed by a plurality of "loops" or "coils" 719 of wire. The inductive charger 706 also comprises an electrical connection 720 to a power source. In one example, the electrical connection includes a galvanic isolation element or a transformer (not shown in FIG. 7) to insulate the power source from the electronics of the inductive charger 706. The electrical connection 720 may also include a 12V DC adapter (not shown in FIG. 7).

In general, the coil excitation system 716 comprises one or more elements (e.g., a waveform generator, one or more amplifiers, tuning capacitors, etc.) that are used to drive the coil assembly 718 with an alternating current signal so that the coil assembly will emit a corresponding magnetic field. That is, when driven by the coil excitation system 716, the wire coils 719 hold varying electrical currents that generate/emit magnetic fields that, as described further below, can be used to inductively charge the external component 704. In certain examples, the coil excitation system 716 and coil assembly 718 are configured to operate in accordance with the Qi open interface standard defining wireless power transfer using inductive charging over distances of up to 4 cm (1.6 inches), developed by the Wireless Power Consortium.

The external component 704 includes, among other elements, a coil assembly 708, a magnet (not shown in FIG. 7), and a rechargeable battery (also not shown in FIG. 7). The external component 704 is configured to be recharged via power received from the inductive charger 706 (via inductive coupling of coil assemblies 708 and 718). As noted, the external component 704 is also configured to send power, and potentially data, to the spinal stimulator 702 (via inductive coupling of coil assemblies 708 and 710).

That is, the external component 704 is configured for wireless communication with the spinal stimulator 702, and for wireless communication with the inductive charger 706. In FIG. 7, the wireless communication between external component 704 and spinal stimulator 702, sometimes referred to herein as a bi-directional "transcutaneous link," is represented by arrow 703. Similarly, the wireless communication between external component 704 and inductive charger 706, sometimes referred to herein as a "charging link," is represented by arrow 705. As described further below, the single coil assembly 708 of external component 704 is used for receiving charging signals (power) from the inductive charger 706 via the charging link 705, as well as for transferring power to, and potentially transferring data and/or receiving data from, the implantable component 702 via transcutaneous link 703.

In practice, the transcutaneous link 703 and the charging link 705 operate at different frequencies, where lower frequencies are typically used for the charging link and higher frequencies are used for the transcutaneous link. For example, transcutaneous link 703 may operate at approximately 5 Megahertz (MHz), at approximately 6.78 MHz, at approximately 13.56 MHz, at approximately 27.12 MHz, etc., while the charging link 705 may operate at approximately less than 400 kilohertz (kHz), as at approximately 140 kHz, at approximately 100 kHz, less than 100 kHz, etc. In accordance with embodiments presented herein, the coil assembly 708 of the external component 704 is configured to selectively operate at both the transcutaneous link frequency and the charging link frequency (i.e., operate in one mode, e.g., 140 kHz Qi WPC, for accepting wireless power charging signals and in another mode operate at, e.g., 5 MHz, 6.8 MHz, etc. for delivering power to the implant). As such, the coil assembly 708 of the external component 704 is sometimes referred to herein as a dual-band wireless power transfer coil assembly or, more simply, as a "dual-band coil assembly."

Although FIG. 7 illustrates both the transcutaneous link 703 and the charging link 705, it is to be appreciated that these two links would be operative at different times. In particular, the transcutaneous link 703 would only be activate and operational when the external component 704 is positioned in close proximity to the implantable component 702, such as when the external component 704 is worn on the head of the recipient. The magnets in the external component 704 and the implantable component 702 may cooperate to retain the external component 704 on the recipient's body and to align the coil assemblies 708 and 710, thereby facilitating the inductive coupling and formation of the transcutaneous link 703.

Conversely, the charging link 705 would only be activate and operational when the external component 704 is positioned in close proximity to the inductive charger 706. For instance, a recipient may remove the external component 704 from his/her body and place the external component 704 on top of the inductive charger 706 so that the coil assemblies 708 and 718 are in close proximity to one another.

In the example of FIG. 7, the dual-band coil assembly 708 of external component 704 comprises a first coil section/segment 724(A), sometimes referred to herein as $L_{1A}$, and a second coil segment/section 724(B), sometimes referred to herein as $L_{1B}$. The external component 704 also comprises a charger detection circuit 726, a coil switch 728, a coil driver 730 (e.g., a 5 MHz, 6.78 Mhz, etc. Class-D/E driver), a battery manager/charging circuit 732 (e.g., Qi-WPC manager), and a rechargeable battery 734. In the example of FIG. 7, the charger detection circuit 726 comprises a sniffer or detection coil segment 736, sometimes referred to herein as $L_2$ or $L_{1C}$, a low pass filter (not shown in FIG. 7), and, in certain embodiments, a threshold detector (also not shown in FIG. 7).

As noted above, dual-band coil assemblies in accordance with embodiments presented herein, such as dual-band coil assembly 708, is operable in first and second modes. In the first mode, sometimes referred to herein as the "battery charging mode," the first coil segment 724(A) and the second coil segment 724(B) have a first electrically connected arrangement that enables the dual-band coil assembly 708 to receive charging signals from an inductive charger (e.g., inductive charger 106), where the charging signals are transmitted/sent at a first frequency. In the second mode, sometimes referred to as the "transcutaneous transfer mode," the first coil segment 724(A) and the second coil segment 724(B) have a second electrically connected arrangement that enables the of the dual-band coil assembly 708 to send/transmit transcutaneous signals (e.g., power and/or data) to an implantable component (e.g. implantable component 102). The transcutaneous signals are transmitted/sent at a second frequency that is different from the first frequency, and the second electrically connected arrangement of the coil segments 724(A) and 724(B) is different from the first electrically connected arrangement of the coil segments 724(A) and 724(B). Each of the battery charging mode and the transcutaneous transfer mode of the dual-band coil assembly 708 are described further below.

More specifically, in the battery charging mode, the coil segments 724(A) and 724(B) are in series resonance to load the battery at a lower frequency (e.g., battery charging at 140 kHz (WPC), where turns $L_{1A}$ and 4 turns $L_{1B}$ are closely coupled to the Qi coil assembly of the inductive charger). During the battery charging mode, coil switch 728 is closed so as to bypass (short) the coil driver 730 to directly connect coil segments 724(A) and 724(B) in series.

The battery charging mode is activated whenever the dual-band coil assembly 708 is inductively coupled to the coil assembly of an inductive charger. The inductive coupling of the dual-band coil assembly 708 is inductively coupled to the coil assembly of an inductive charger is detected by the charger detection circuit 726. More specifically, when a user places the external component 704 on top of an inductive charger, the detection coil segment 736 will be exposed to the electromagnetic field generated by the inductive charger. As such, current signals will be induced in the detection coil segment 736 and these current signals are provided to low pass filter 738.

As noted above, the charging signals (electromagnetic field generated by the inductive charger) are associated with lower frequencies (e.g., 140 kHz), while the transcutaneous signals (electromagnetic fields generated by the OTE component 704 and/or an implantable component) are associated with higher frequencies (e.g., 5 Mhz, 6.78 Mhz, etc.). Therefore, the current signals induced in the detection coil segment 736 by the inductive charger will have a corresponding lower frequency (e.g., 140 kHz). The low pass filter in the charger detection circuit 726 has an upper cut-off frequency that is sufficiently high so as to enable these lower frequency current signals to pass there through, but also which is low enough to block any current signals induced in the detection coil segment 736 as result of transcutaneous communication (e.g., block 5 Mhz, 6.78 Mhz, etc. signals induced by electromagnetic fields generated by the OTE component 704 and/or an implantable component).

Once the induced signals at detection coil segment 736 pass through the low pass filter and the threshold detector (if present), the induced signals are rectified to direct current (DC) (e.g., at threshold detector or at a separate rectifier) and provided to the coil switch 728. The DC current generated by the induced signals causes the coil switch 728 to close and, as noted above, connect coil segments 724(A) and 724(B) together in series. As such, the coil switch 728 is powered by current drawn from the inductive charger via detection coil segment 736. In this way, even if the battery 734 is empty, the coil switch 728 can still close so as to directly connect dual-band coil assembly 708 (i.e., the turns of $L_{1A}$ and the turns $L_{1B}$) to the battery manager 732, utilizing mainly a series resonance circuit (i.e., with the $C_{T\_WPC}$ capacitors 745(A) and 745(B)). Moreover, as noted above, coil switch 728 is only closed when the external component 704 is placed on the inductive charger and not when the detection coil segment 736 are exposed to electromagnetic fields generated by the external component 704 itself and/or spinal cord stimulator 702.

Stated differently, the coil switch 728 is driven by a third (floating) coil (detection coil segment 736) that extracts the electromagnetic field (e.g., 140 kHz field) from the inductive charger. Removing the external component 704 from the inductive charger automatically opens the coil switch 728. The coil switch 728 may comprise, for example, one or more Metal Oxide Semiconductor Field Effect Transistors (MOSFETs), one or more bipolar transistors, microelectromechanical system (MEMS) coil switch, an optocoupler, miniature electro-mechanic coil switch, etc.

As noted above, the detection coil segment 736 are used to detect the presence of the inductive charger and to obtain signals that are used to close the coil switch 728. The detection coil segment 736 is galvanically insulated from coil segments 724(A) and 724(B) (i.e., electrically floating relative to segments 724(A) and 724(B)), although coil segments 724(A), 724(B) and detection coil segment 736 may be part of the same coil geometry and are located proximate to one another (e.g., all are well magnetically coupled and at the same surface of the external component 704).

In certain embodiments, the detection coil segment 736 also functions as a dampening coil used during the transcutaneous communication with an implantable component. In such embodiments, the detection coil segment 736 is used, during transcutaneous communication to optimize the integrity of the near-field communication link over a large range of recipient skin flap thicknesses (i.e., used to lower the "Q" during data/power transfer with an implantable component).

As noted, in addition to the battery charging mode described above, the dual-band coil assembly 708 is also operable in a transcutaneous transfer mode when the dual-band coil assembly 708 is closely coupled to implantable coil assembly 710). As such, during the transcutaneous transfer mode, the first coil segment 724(A) and the second coil segment 724(B) have a second electrically connected arrangement that enables the of the dual-band coil assembly 708 to send/transmit transcutaneous signals (e.g., power and/or data) to the spinal cord stimulator 702. In the transcutaneous transfer mode, coil segments 724(A) and 724(B) are oppositely coupled to one another seen from the coil driver 730 (e.g., coupled together at a center point via the coil driver).

The transcutaneous transfer mode is activated in the presence of an implantable component (i.e., when dual-band coil assembly 208 is inductively coupled to the implantable coil assembly 710) and once the battery 734 is sufficiently charged. The inductive coupling to spinal cord stimulator 702 does not need to be detected since the coil switch 728 is default open. That is, when a user removes the external component 704 from the top of an inductive charger 706, the coil switch 728 opens to connect remove the bypass of coil driver 730.

More specifically, as noted above, the charging signals (electromagnetic field generated by the inductive charger) are associated with lower frequencies (e.g., 140 kHz), while the transcutaneous signals (electromagnetic fields generated by the external component 704 and/or spinal cord stimulator 702) are associated with higher frequencies (e.g., 5 Mhz, 6.78 Mhz, etc.). Therefore, any current or voltage signals induced in the detection coil segment 736 during transcutaneous transfer will be above the upper cut-off frequency of low pass filter in the charger detection circuit 726. Accordingly, the signals will be blocked by the low pass filter and/or the threshold detector (if present), and the coil switch 728 will unpowered (open) (i.e., the low-pass filter prevents that fields at 5 MHz or 6.78 MHz from closing the coil switch 728 and the 5 MHz or 6.78 MHz coil driver 730 becomes active).

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   detecting presence of charging signals at a coil assembly of an external component of an implantable medical device system, wherein the coil assembly comprises first and second coil segments;
   in response to detection of the charging signals at the coil assembly, actuating at least one coil switch to place the coil assembly in a first electrically connected arrangement;
   receiving, via the coil assembly in the first electrically connected arrangement, charging signals sent by an inductive charger at a first frequency;
   detecting that the charging signals are not present at the coil assembly;
   in response to detection of the absence of the charging signals, actuating the at least one coil switch to place the coil assembly in a second electrically connected arrangement; and
   sending, via the coil assembly in the second electrically connected arrangement, transcutaneous signals from the external component to an implantable component at a second frequency,
   wherein the second electrically connected arrangement is different from the first electrically connected arrangement and wherein the second frequency is different from the first frequency.

2. The method of claim 1, further comprising:
providing the charging signals to a battery charger of the external component for use in charging a rechargeable battery of the external component; and
obtaining, at a coil driver of the external component, power from the rechargeable battery, wherein the power obtained from the rechargeable battery is used to transmit the transcutaneous signals from the external component to the implantable component.

3. The method of claim 1, further comprising:
in response to detecting of the charging signals at the coil assembly, automatically closing the at least one coil switch of the external component to connect the first and second coil segments in series so as to form the first electrically connected arrangement.

4. The method of claim 3, wherein the coil assembly comprises a detection coil segment that is galvanically isolated from the first and second coil segments, and wherein the method further comprises:
powering the at least one coil switch via voltage or current signals induced in the detection coil segment.

5. The method of claim 4, further comprising:
low pass filtering the signals detected at the detection coil segment.

6. The method of claim 1, wherein the external component comprises a coil driver, and wherein the method further comprises:
in response to detecting that the charging signals are not present at the coil assembly, automatically opening the at least one coil switch such that the first and second coil segments are differentially connected to the coil driver so as to form the second electrically connected arrangement.

7. The method of claim 1, further comprising:
in response to detection that the charging signals are not present at the coil assembly, actuating the at least one coil switch such that the first and second coil segments are connected in parallel so as to form the second electrically connected arrangement.

8. The method of claim 1, wherein sending transcutaneous signals from the external component to the implantable component at the second frequency, comprises:
sending power signals to the implantable component.

9. The method of claim 1, wherein sending transcutaneous signals from the external component to the implantable component at the second frequency, comprises:
sending power and data signals to the implantable component.

10. The method of claim 1, further comprises:
receiving, via the coil assembly in the second electrically connected arrangement, transcutaneous signals from the implantable component at the second frequency.

11. An external component of an implantable medical device system, comprising:
a coil assembly comprising a first coil segment and a second coil segment;
a coil driver;
a rechargeable battery;
a battery manager;
at least one coil switch configured to, in response to receipt of low frequency charging signals at the coil assembly, automatically close so as to connect the first and second coil segments in series to provide the low frequency charging signals to the battery manager for use in recharging the rechargeable battery; and
a charger detection circuit configured to automatically close the at least one coil switch in response to receipt of the low frequency charging signals at the coil assembly, wherein the charger detection circuit comprises a detection coil segment that is galvanically isolated from the first and second coil segments, and wherein the at least one coil switch is powered via signals detected at the detection coil segment.

12. The external component of claim 11, wherein the detection coil segment is configured to receive high frequency transcutaneous signals that are at least one of sent or received by the first and second coil segments, and wherein the charger detection circuit comprises:
a low pass filter configured to prevent the at least one coil switch from closing in receipt of the high frequency transcutaneous signals at the detection coil segment.

13. The external component of claim 11, wherein when low frequency charging signals are not received at the coil assembly, the charger detection circuit is configured to automatically open the at least one coil switch.

14. The external component of claim 11, wherein when low frequency charging signals are not received at the coil assembly, the at least one coil switch is configured to automatically open such that the first and second coil segments are electrically connected in a second arrangement, and wherein the coil driver is configured to transmit, via the first and second coil segments, transcutaneous signals from the external component to an implantable component at a second frequency that is higher than a first frequency associated with the low frequency charging signal.

15. The external component of claim 14, wherein in the second arrangement, the first and second coil segments are differentially connected to the coil driver.

16. The external component of claim 14, wherein in the second arrangement, the first and second coil segments are connected in parallel with one another.

17. The external component of claim 14, wherein the transcutaneous signals comprise one or more of power signals or data signals.

18. The external component of claim 11, wherein the first and second coil segments are concentric coils.

19. An external component of an implantable medical device system, comprising:
a coil assembly comprising a first coil segment, a second coil segment, and a detection coil segment;
a charger detection circuit configured to detect presence of signals below a first frequency at the detection coil segment; and
at least one controllable switch configured to close when the charger detection circuit detects the presence of signals below the first frequency at the detection coil segment so as to connect the first and second coil segments in a first electrically connected arrangement, wherein the first and second coil segments in the first electrically connected arrangement are configured to receive charging signals sent by an inductive charger at the first frequency,
wherein the at least one controllable switch is configured to be default open when the charger detection circuit does not detect the presence of signals below the first frequency at the detection coil segment such that so the first and second coil segments are connected in a second electrically connected arrangement, wherein the first and the second coil segments in the second electrically connected arrangement are configured to send transcutaneous signals to an implantable component at a second frequency.

20. The external component of claim 19, wherein the detection coil segment is galvanically isolated from the first and second coil segments, and wherein the at least one controllable switch is powered via voltage or current signals induced in the detection coil segment.

21. The external component of claim 19, wherein in the first electrically connected arrangement the first and second coil segments are connected in series via the at least one controllable switch.

22. The external component of claim 19, wherein the external component comprises a coil driver, and wherein in the second electrically connected arrangement the first and second coil segments are differentially connected to the coil driver.

23. The external component of claim 19, wherein in the second electrically connected arrangement the first and second coil segments are connected in parallel with one another.

* * * * *